United States Patent
L'Alloret

(10) Patent No.: US 7,316,809 B2
(45) Date of Patent: Jan. 8, 2008

(54) AQUEOUS PHOTOPROTECTIVE COMPOSITIONS COMPRISING DIBLOCK OR TRIBLOCK COPOLYMERS AND 4,4-DIARYLBUTADIENE UV-A SUNSCREENS

(75) Inventor: Florence L'Alloret, Paris (FR)

(73) Assignee: L'Oreal, Paris (FR)

( * ) Notice: Subject to any disclaimer, the term of this patent is extended or adjusted under 35 U.S.C. 154(b) by 798 days.

(21) Appl. No.: 10/823,659

(22) Filed: Apr. 14, 2004

(65) Prior Publication Data
US 2004/0223924 A1 Nov. 11, 2004

Related U.S. Application Data

(60) Provisional application No. 60/468,060, filed on May 6, 2003.

(30) Foreign Application Priority Data

Apr. 14, 2003 (FR) .................... 03 04646

(51) Int. Cl.
*A61Q 17/04* (2006.01)
*A61Q 19/00* (2006.01)
*A61K 8/00* (2006.01)

(52) U.S. Cl. .................... 424/59; 424/60; 424/400; 424/401

(58) Field of Classification Search .................... 424/59, 424/60, 400, 401
See application file for complete search history.

(56) References Cited

U.S. PATENT DOCUMENTS

| 4,804,531 A | 2/1989 | Grollier |
| 6,093,385 A | 7/2000 | Habeck et al. |
| 2003/0059391 A1 | 3/2003 | L'Alloret |
| 2003/0059392 A1 | 3/2003 | L'Alloret |

FOREIGN PATENT DOCUMENTS

| JP | 7-330567 | 12/1995 |
| JP | 2001-288233 | 10/2001 |
| WO | 02/49596 A2 | 6/2002 |

OTHER PUBLICATIONS

French Search Report Issued in French Priority Counterpart FR 03/04646, on Dec. 10, 2003, 2 pages.
Tamura, Hiroaki, Fragrance Journal, Aug. 1998, pp. 79-83.
Japanese Notice of Rejection issued in counterpart Japanese Patent Application No. 2004-119675 issued Jun. 21, 2005, 3 pages.

*Primary Examiner*—Shelley A. Dodson
(74) *Attorney, Agent, or Firm*—Buchanan, Ingersoll & Rooney, PC

(57) ABSTRACT

Photoprotective compositions, e.g., oil-in-water or water-in-oil emulsions, well suited for the photoprotection of the skin, lips and/or hair against the damaging effects of UV-radiation, comprise at least one aqueous phase, at least one water-soluble or water-dispersible polymer having a diblock structure A-B or a triblock structure B-A-B wherein A is an ionic water-soluble polymeric block and B is a hydrophobic polymeric block and at least one system screening out UV radiation, said at least one screening system comprising at least one 4,4-diarylbutadiene UV-A screening agent.

42 Claims, No Drawings

AQUEOUS PHOTOPROTECTIVE COMPOSITIONS COMPRISING DIBLOCK OR TRIBLOCK COPOLYMERS AND 4,4-DIARYLBUTADIENE UV-A SUNSCREENS

CROSS-REFERENCE TO PRIORITY/PROVISIONAL APPLICATIONS

This application claims priority under 35 U.S.C. § 119 of FR-03/04646, filed Apr. 14, 2003, and of provisional application Ser. No. 60/468,060, filed May 6, 2003, both hereby expressly incorporated by reference and both assigned to the assignee hereof. This application is also a continuation of said '060 provisional.

BACKGROUND OF THE INVENTION

1. Technical Field of the Invention

The invention relates to photoprotective compositions comprising at least one aqueous phase, at least one water-soluble or water-dispersible polymer having a diblock structure A-B or a triblock structure B-A-B wherein A is an ionic water-soluble polymeric block and B is a hydrophobic polymeric block and at least one system screening out UV radiation, said screening system comprising at least one UV-A screening agent of the 4,4-diarylbutadiene type.

2. Description of Background and/or Related and/or Prior Art

It is well known that light radiation having wavelengths of between 280 nm and 400 nm allows tanning of the human epidermis, and that rays having wavelengths of between 280 nm and 320 nm, known by the name UV-B, cause erythemas and skin burns which can hamper the development of the natural tan; this UV-B radiation must therefore be screened out.

It is also known that UV-A rays having wavelengths of between 320 nm and 400 nm, which cause tanning of the skin, are capable of inducing its impairment, in particular in the case of a sensitive skin or a skin continually exposed to solar radiation. UV-A rays cause in particular a loss of elasticity of the skin and the appearance of wrinkles which lead to premature aging. They promote the onset of the erythematous reaction or amplify this reaction in some subjects and may even be responsible for phototoxic or photoallergic reactions. It is therefore desirable to also screen out UV-A radiation.

UV-A and UV-B rays must therefore be screened out and cosmetic compositions protecting the human epidermis, containing UV-A and UV-B screening agents currently exist.

These anti-sun compositions exist either in the form of an aqueous lotion or serum containing no fatty phase, or in the form of an emulsion of the oil-in-water type (that is to say a cosmetically and/or dermatologically acceptable carrier consisting of an aqueous dispersive continuous phase and a fatty dispersed discontinuous phase) or water-in-oil type (aqueous phase dispersed in a continuous fatty phase), which contain, in various concentrations, one or more fat-soluble conventional organic screening agents and/or water-soluble conventional organic screening agents capable of selectively absorbing harmful UV radiation, these screening agents (and their quantities) being selected according to the desired sun protection factor, the sun protection factor (SPF) being mathematically expressed by the ratio of the dose of UV radiation necessary to reach the erythematogenic threshold with a UV-screening agent to the dose of UV radiation necessary to reach the erythematogenic threshold without UV-screening agent. In such emulsions, the hydrophilic screening agents are present in the aqueous phase and the lipophilic screening agents are present in the fatty phase. Multiple emulsions also exist which are obtained after dispersing an invert emulsion in an aqueous phase.

There are known from EP-1,279,398 and EP-1,281,395 water-soluble or water-dispersible polymers, having a diblock structure A-B or triblock structure B-A-B, where A is an ionic water-soluble polymeric block and B a hydrophobic polymeric block, which are particularly advantageous because they exhibit gelling properties of water in low concentrations (less than 1%) and make it possible to stabilize surfactant-free emulsions, having nice textures.

These polymers can therefore be used in the following main galenic carriers:

(a) aqueous lotions or serums comprising no fatty phase, as gelling agents, (b) emulsions which are dispersions of two immiscible liquids such as water and oil, as emulsifying and/or gelling agents. There can be distinguished direct emulsions comprising an oily phase dispersed in an aqueous phase, invert emulsions being dispersions of an aqueous phase in an oily phase. Multiple emulsions also exist which are obtained after dispersion of an invert emulsion in an aqueous phase.

The block polymers have the advantage of giving compositions having good safety towards the skin because they are free of small-sized surfactant molecules. They make it possible moreover, to obtain a broader range of textures than the commonly used gelling compounds (crosslinked hydrophilic polymers such as the Carbopols provided by Noveon, natural polymers such as xanthan gum) whose amphiphilic character is not sufficient to introduce contents of oil greater than 10%.

Among the available organic UV-A screening agents, a family of compounds which are particularly effective in UV-A is 1,4-benzene[di(3-methylidene-10-camphorsulfonic)] acid and its different salts, which is described in FR-A-2,528,420 and FR-A-2,639,347; they are indeed capable of absorbing ultraviolet rays having wavelengths of between 280 nm and 400 nm, with absorption maxima of between 320 nm and 400 nm, in particular in the region of 345 nm.

In the laboratories of the assignee hereof, it has been observed that the introduction of this type of UV-A-screening agent into sunscreening aqueous compositions gelled and/or stabilized with water-soluble or water-dispersible polymers, having a diblock structure A-B or a triblock structure B-A-B, can induce a reduction in their viscosity or their destabilization.

It thus appears necessary to have aqueous compositions based on water-soluble or water-dispersible polymers, having a diblock structure A-B or a triblock structure B-A-B which are stable in a broad range of possible consistencies and which can contain organic screening agents active in UV-A, of comparable efficacy to that of 1,4-benzene[di(3-methylidene-10-camphorsulfonic)] acid and its various salts without the disadvantages listed above.

SUMMARY OF THE INVENTION

It has now surprisingly and unexpectedly been determined that aqueous anti-sun (sunscreen) compositions comprising at least one water-soluble or water-dispersible polymer, having a diblock structure A-B or a triblock structure B-A-B and at least one UV-A screening agent of the 4,4-diarylbutadiene type ameliorate or avoid the above disadvantages and drawbacks.

In the remainder of the present description, the expression "system screening out UV radiation" is understood to mean an agent screening out UV radiation comprising either a single organic or inorganic compound screening out UV radiation or a mixture of several organic or inorganic compounds screening out UV radiation, for example the mixture comprising a UV-A screening agent and a UV-B screening agent.

This discovery forms the basis of the present invention.

The present invention thus features photoprotective compositions comprising at least one aqueous phase, at least one water-soluble or water-dispersible polymer having a diblock structure A-B or a triblock structure B-A-B where A is an ionic water-soluble polymeric block and B is a hydrophobic polymeric block and at least one system screening out UV radiation, said screening system comprising at least one UV-A screening agent of the 4,4-diarylbutadiene type.

Other characteristics, aspects and advantages of the invention will be seen from the detailed description which follows.

The expression "stable" is understood to mean that the macroscopic and microscopic appearance of the composition is not modified after 1 month at room temperature.

The expression "water-soluble or water-dispersible" is understood to mean polymers which, when introduced into an aqueous phase at 25° C., at a concentration by mass equal to 1%, allow a macroscopically homogeneous transparent solution to be obtained, that is to say having a maximum light transmittance value, at a wavelength equal to 500 nm, through a sample 1 cm thick, of at least 60%, preferably of at least 70%.

The expression "polymeric" is understood to mean a block whose molar mass is greater than 400 g/mol, and preferably greater than 800 g/mol.

The expression "hydrophobic" is understood to mean a block which, when introduced into a hydrocarbon solvent at 25° C., at a concentration by mass equal to 1%, allows a macroscopically homogeneous and transparent solution to be obtained, that is to say having a maximum light transmittance value, at a wavelength equal to 500 nm, through a sample 1 cm thick, of at least 70%, preferably of at least 80%. The hydrocarbon solvent has a dielectric constant measured at 25° C. of less than 50; this solvent may be chosen in particular from alkanes such as cyclohexane (dielectric constant: 2.02), aromatic solvents such as ethylbenzene (dielectric constant: 2.4), ketones such as cyclohexanone (dielectric constant: 18.3), alcohols such as cyclohexanol (dielectric constant: 15.0), chlorinated hydrocarbon solvents such as dichloromethane (dielectric constant: 9.08), amides such as dimethylformamide and esters such as ethyl acetate (dielectric constant: 6.02).

DETAILED DESCRIPTION OF BEST MODE AND SPECIFIC/PREFERRED EMBODIMENTS OF THE INVENTION

The ionic water-soluble block A of the polymers of the invention is obtained from one or more water-soluble monomers (Ia) or salts thereof, such as for example:
(meth)acrylic acid,
styrenesulfonic acid,
vinylsulfonic acid and (meth)allylsulfonic acid,
vinylphosphonic acid,
maleic acid,
itaconic acid,
crotonic acid,
dimethyldiallylammonium chloride,
methylvinylimidazolium chloride,
ethylenic carboxybetaines or sulfobetaines obtained for example by quaternization of ethylenically unsaturated monomers containing an amine function group, with sodium salts of carboxylic acid having an active halogen (e.g.,: chloroacetate) or with cyclic sulfones (e.g.,: propane sulfone),
water-soluble vinyl monomers of the following formula (A):

in which $R_1$ is H, $-CH_3$, $-C_2H_5$ or $-C_3H_7$ and $X_1$ is selected from the group consisting of:

(i) alkyl oxides of the $-OR_2$ type wherein $R_2$ is a saturated or unsaturated, linear or branched hydrocarbon radical having from 1 to 6 carbon atoms, substituted with at least one sulfonic ($-SO_3^-$) and/or sulfate ($-SO_4^-$) and/or phosphate ($-PO_4H_2^-$) and/or quaternary ammonium ($-N^+R_3R_4R_5$) group in which $R_3$, $R_4$ and $R_5$, which may be identical or different, are each a saturated or unsaturated, linear or branched hydrocarbon radical having 1 to 6 carbon atoms, provided that the sum of the carbon atoms of $R_2+R_3+R_4+R_5$ does not exceed 6. The radical $R_2$ is optionally substituted with a halogen atom (iodine, bromine, chlorine, fluorine); hydroxyl ($-OH$); ether ($-O-$), primary amine ($-NH_2$); secondary amine ($-NHR_6$) and/or tertiary amine ($-NR_6R_7$) in which $R_6$ and $R_7$, which may be identical or different, are each a saturated or unsaturated, linear or branched hydrocarbon radical having 1 to 6 carbon atoms, provided that the sum of the carbon atoms of $R_2+R_6+R_7$ does not exceed 6. Exemplary is quaternized dimethylaminoethyl methacrylate (DAMEMA);

(ii) $-NH_2$, $-NHR_8$ and $-NR_8R_9$ radicals in which $R_8$ and $R_9$, which may be identical or different, are each a saturated or unsaturated, linear or branched hydrocarbon radical having 1 to 6 carbon atoms, provided that the total number of carbon atoms of $R_8+R_9$ does not exceed 6, the said $R_8$ and/or $R_9$ being substituted with at least one sulfonic ($-SO_3^-$) and/or sulfate ($-SO_4^-$) and/or phosphate ($-PO_4H_2^-$) and/or quaternary amine ($-N+R_{10}R_{11}R_{12}$) group in which $R_{10}$, $R_{11}$ and $R_{12}$, which may be identical or different, are each a saturated or unsaturated, linear or branched hydrocarbon radical having 1 to 6 carbon atoms, provided that the sum of the carbon atoms of $R_8+R_9+R_{10}+R_{11}+R_{12}$ does not exceed 6. The radicals $R_8$ and/or $R_9$ are optionally substituted with a halogen atom (iodine, bromine, chlorine, fluorine); a hydroxyl group ($-OH$); an ether group ($-O-$), a primary amine group ($-NH_2$); a secondary amine group ($-NHR_{13}$) and/or a tertiary amine group ($-NR_{13}R_{14}$) in which $R_{13}$ and $R_{14}$, which may be identical or different, are each a saturated or unsaturated, linear or branched hydrocarbon radical having 1 to 6 carbon atoms, provided that the sum of the carbon atoms of $R_8+R_9+R_{13}+R_{14}$ does not exceed 6. Exemplary are acrylamido-2-methylpropanesulfonic acid (AMPS), (meth)acrylamidopropyltrimethylammonium chloride (APTAC and MAPTAC).

The ionic water-soluble block A may also contain one or more neutral water-soluble monomers (Ib), such as for example:
(meth)acrylamide,
N-vinylacetamide and N-methyl-N-vinylacetamide, N-vinylformamide and N-methyl-N-vinylformamide, maleic anhydride, vinylamine, N-vinyllactams containing a cyclic alkyl group having from 4 to 9 carbon atoms, such as N-vinylpyrrolidone, N-butyrolactam and N-vinylcaprolactam, vinyl alcohol of formula $CH_2=CHOH$, water-soluble vinyl monomers of the following formula (B):

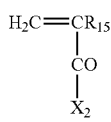

in which $R_{15}$ is chosen from H, $-CH_3$, $-C_2H_5$ or $-C_3H_7$ and $X_2$ is selected from the group consisting of:

(i) alkyl oxides of $-OR_{16}$ type wherein $R_{16}$ is a saturated or unsaturated, linear or branched hydrocarbon radical having from 1 to 6 carbons, optionally substituted with a halogen atom (iodine, bromine, chlorine, fluorine); a hydroxyl group (—OH); an ether group (—O—); a primary amine group ($-NH_2$); a secondary amine group ($-NHR_{17}$) and/or a tertiary amine group ($-NR_{17}R_{18}$) in which $R_{17}$ and $R_{18}$, which may be identical or different, are each a saturated or unsaturated, linear or branched hydrocarbon radical having 1 to 6 carbon atoms, provided that the sum of the carbon atoms of $R_{16}+R_{17}+R_{18}$ does not exceed 6. Exemplary are glycidyl (meth)acrylate, hydroxyethyl methacrylate, and ethylene glycol, diethylene glycol or polyalkylene glycol (meth)acrylates;

(ii) the $-NH_2$, $-NHR_{19}$ and $-NR_{19}R_{20}$ radicals in which $R_{19}$ and $R_{20}$, which may be identical or different, are each saturated or unsaturated, linear or branched hydrocarbon radical having 1 to 6 carbon atoms, provided that the total number of carbon atoms of $R_{19}+R_{20}$ does not exceed 6, the said $R_{19}$ and $R_{20}$ being optionally substituted with a halogen atom (iodine, bromine, chlorine, fluorine); a hydroxyl group (—OH); an ether group (—O—); a primary amine group ($-NH_2$); a secondary amine group ($-NHR_{21}$) and/or a tertiary amine group ($-NR_{21}R_{22}$) with $R_{21}$ and $R_{22}$, which may be identical or different, are each a saturated or unsaturated, linear or branched hydrocarbon radical having 1 to 6 carbon atoms, provided that the sum of the carbon atoms of $R_{19}+R_{20}+R_{21}+R_{22}$ does not exceed 6. Exemplary is dimethylaminoethylmethacrylamide.

The ionic water-soluble block A of the polymers of the invention may also contain one or more hydrophobic monomers (Ic), the said hydrophobic monomers being present in a sufficiently low quantity for the block A to be soluble in water.

There may be mentioned, for example, as hydrophobic monomers (Ic):

styrene and its derivatives such as 4-butylstyrene, alpha-methylstyrene and vinyltoluene, vinyl acetate of formula $CH_2=CH-OCOCH_3$, vinyl ethers of formula $CH_2=CHOR$ in which R is a saturated or unsaturated, linear or branched hydrocarbon radical having from 1 to 6 carbon atoms, acrylonitrile, caprolactone, vinyl chloride and vinylidene chloride, silicone derivatives, after polymerization providing silicone polymers such as methacryloxypropyltris(trimethylsiloxy)silane and silicone methacrylamides, hydrophobic vinyl monomers of the following formula (C):

in which $R_{23}$ is H, $-CH_3$, $-C_2H_5$ or $-C_3H_7$ and $X_3$ is selected from the group consisting of:

(i) alkyl oxides of the $-OR_{24}$ type wherein $R_{24}$ is a saturated or unsaturated, linear or branched hydrocarbon radical having from 1 to 6 carbons;

(ii) the $-NH_2$, $-NHR_{25}$ and $-NR_{25}R_{26}$ radicals in which $R_{25}$ and $R_{26}$, which may be identical or different, are each a saturated or unsaturated, linear or branched hydrocarbon radical having 1 to 6 carbon atoms, provided that the total number of carbon atoms of $R_{25}+R_{26}$ does not exceed 6. Exemplary are methyl methacrylate, ethyl methacrylate, n-butyl (meth)acrylate, tert-butyl (meth)acrylate, cyclohexyl acrylate and isobornyl acrylate and 2-ethylhexyl acrylate.

The ionic water-soluble block A may also be polyethyleneimine.

The ionic water-soluble block A is completely or partially neutralized with an inorganic or organic base. This base may be selected, for example, from among the salts of sodium, ammonium, lithium, calcium, magnesium and ammonium substituted with 1 to 4 alkyl radicals having from 1 to 15 carbon atoms, or alternatively from mono-, di-, and triethanolamine, aminoethylpropanediol, N-methylglucamine, and basic amino acids such as arginine and lysine, and mixtures thereof.

The hydrophobic block B is obtained from hydrophobic monomers (Id), such as, for example:

styrene and its derivatives such as 4-butylstyrene, alpha-methylstyrene and vinyltoluene, vinyl acetate of formula $CH_2=CH-OCOCH_3$, vinyl ethers of formula $CH_2=CHOR'$ in which R' is a saturated or unsaturated, linear or branched hydrocarbon radical having from 1 to 6 carbons, acrylonitrile, vinyl chloride and vinylidene chloride, caprolactone, alkenes such as ethylene, propylene, butylene and butadiene, silicone derivatives, after polymerization providing silicone polymers such as polydimethylsiloxane, methacryloxypropyltris(trimethylsiloxy)silane and silicone methacrylamides, hydrophobic vinyl monomers of the following formula (D):

in which $R_{27}$ is H, —$CH_3$, —$C_2H_5$ or —$C_3H_7$ and $X_4$ is selected from the group consisting of:

(i) alkyl oxides of the —$OR_{28}$ type wherein $R_{28}$ is a saturated or unsaturated, linear or branched hydrocarbon radical having from 1 to 22 carbons, optionally substituted with a halogen atom (iodine, bromine, chlorine, fluorine); a sulfonic group (—$SO_3^-$), a sulfate group (—$SO_4^-$), a phosphate group (—$PO_4H_2^-$); a hydroxyl group (—OH); an ether group (—O—); a primary amine group (—$NH_2$); a secondary amine group (—$NHR_{29}$) and/or a tertiary amine group (—$NR_{29}R_{30}$) or a quaternary amine group (—$N^+R_{29}R_{30}R_{31}$) in which $R_{29}$, $R_{30}$ and $R_{31}$, which may be identical or different, are each a saturated or unsaturated, linear or branched hydrocarbon radical having 1 to 22 carbon atoms, provided that the sum of the carbon atoms of $R_{28}+R_{29}+R_{30}+R_{31}$ does not exceed 22. Exemplary are methyl methacrylate, ethyl methacrylate, n-butyl (meth)acrylate, tert-butyl (meth)acrylate, cyclohexyl acrylate and isobornyl acrylate and 2-ethylhexyl acrylate. $R_{28}$ may also be a perfluoroalkyl radical, preferably a $C_{1-18}$. Exemplary are ethyl perfluorooctyl acrylate and trifluoromethyl (meth)acrylate;

(ii) —$NH_2$, —$NHR_{32}$ and —$NR_{32}R_{33}$ radicals in which $R_{32}$ and $R_{33}$, which may be identical or different, are each a saturated or unsaturated, linear or branched hydrocarbon radical having 1 to 22 carbon atoms, provided that the total number of carbon atoms of $R_{32}+R_{33}$ does not exceed 22, the said $R_{32}$ and $R_{33}$ being optionally substituted with a halogen atom (iodine, bromine, chlorine, fluorine); a hydroxyl group (—OH); an ether group (—O—); a sulfonic group (—$SO_3^-$); a sulfate group (—$SO_4^-$); a phosphate group (—$PO_4H_2^-$); a primary amine group (—$NH_2$); a secondary amine group (—$NHR_{34}$) and/or a tertiary amine group (—$NR_{34}R_{35}$) and/or a quaternary amine group (—$N^+R_{34}R_{35}R_{36}$) in which $R_{34}$, $R_{35}$ and $R_{36}$, which may be identical or different, are each a saturated or unsaturated, linear or branched hydrocarbon radical having 1 to 22 carbon atoms, provided that the sum of the carbon atoms of $R_{32}+R_{33}+R_{34}+R_{35}+R_{36}$ does not exceed 22. $R_{32}$ and $R_{33}$ may also be perfluoroalkyl radicals, preferably a $C_{1-18}$.

The hydrophobic block B of the polymers of the invention may also contain water-soluble monomers (Ie), the said water-soluble monomers being present in a sufficiently low quantity for the block B to be hydrophobic.

There may be mentioned, for example, as water-soluble monomers (Ie) and the salts thereof:

(meth)acrylic acid, styrenesulfonic acid, vinylsulfonic acid and (meth)allylsulfonic acid, vinylphosphonic acid, maleic acid and anhydride, itaconic acid, crotonic acid, dimethyldiallylammonium chloride, methylvinylimidazolium chloride, (meth)acrylamide, N-vinylacetamide and N-methyl-N-vinylacetamide, N-vinylformamide and N-methyl-N-vinylformamide, N-vinyllactams containing a cyclic alkyl group having from 4 to 9 carbon atoms, such as N-vinylpyrrolidone, N-butyrolactam and N-vinylcaprolactam, the vinyl alcohol of formula $CH_2$=CHOH, 2-vinylpyridine and 4-vinylpyridine, water-soluble vinyl monomers of the following formula (E):

$$H_2C=CR_{37}$$
$$|$$
$$CO$$
$$|$$
$$X_5$$

(E)

in which $R_{37}$ is H, —$CH_3$, —$C_2H_5$ or —$C_3H_7$ and $X_5$ is selected from the group consisting of:

(i) alkyl oxides of the —$OR_{38}$ type wherein $R_{38}$ is a saturated or unsaturated, linear or branched hydrocarbon radical having from 1 to 6 carbon atoms, optionally substituted with a halogen atom (iodine, bromine, chlorine, fluorine); a sulfonic group (—$SO_3^-$); a sulfate group (—$SO_4^-$); a phosphate group (—$PO_4H_2^-$); a hydroxyl group (—OH); an ether group (—O—); a primary amine group (—$NH_2$); a secondary amine group (—$NHR_{39}$) and/or a tertiary amine group (—$NR_{39}R_{40}$) or a quaternary ammonium group (—$N^+R_{39}R_{40}R_{41}$) in which $R_{39}$, $R_{40}$ and $R_{41}$, which may be identical or different, are each a saturated or unsaturated, linear or branched hydrocarbon radical having 1 to 6 carbon atoms, provided that the sum of the carbon atoms $R_{38}+R_{39}+R_{40}+R_{41}$ does not exceed 6. Exemplary are quaternized dimethylaminoethyl methacrylate (DAMEMA), glycidyl (meth)acrylate, hydroxyethyl methacrylate, and ethylene glycol, diethylene glycol or polyalkylene glycol (meth) acrylates;

(ii) The —$NH_2$, —$NHR_{42}$ and —$NR_{42}R_{43}$ radicals in which $R_{42}$ and $R_{43}$, which may be identical or different, are each a saturated or unsaturated, linear or branched hydrocarbon radical having 1 to 6 carbon atoms, provided that the total number of carbon atoms of $R_{42}+R_{43}$ does not exceed 6, the said $R_{42}$ and/or $R_{43}$ being optionally substituted with a halogen atom (iodine, bromine, chlorine, fluorine); a sulfonic group (—$SO_3^-$); a sulfate group (—$SO_4^-$); a phosphate group (—$PO_4H_2^-$); a hydroxyl group (—OH); an ether group (—O—); a primary amine group (—$NH_2$); a secondary amine group (—$NHR_{44}$) and/or a tertiary amine group (—$NR_{44}R_{45}$) or a quaternary amine group (—$N^+R_{44}R_{45}R_{46}$) in which $R_{44}$, $R_{45}$ and $R_{46}$, which may be identical or different, are each a saturated or unsaturated, linear or branched hydrocarbon radical having 1 to 6 carbon atoms, provided that the sum of the carbon atoms of $R_{42}+R_{43}+R_{44}+R_{45}+R_{46}$ does not exceed 6. Exemplary are N,N-dimethylacrylamide, acrylamido-2-methylpropanesulfonic acid (AMPS), (meth)acrylamidopropyltrimethylammonium chloride (APTAC and MAPTAC).

The diblock or triblock polymers of the invention preferably have a molar mass of between 1000 g/mol and 500 000 g/mol, preferably between 2000 g/mol and 100 000 g/mol. The ionic water-soluble block A has a molar mass of between 600 g/mol and 300 000 g/mol, preferably between 1200 g/mol and 60 000 g/mol. The hydrophobic block B has a molar mass of between 400 g/mol and 200 000 g/mol, preferably between 800 g/mol and 40 000 g/mol.

The proportion by mass of the ionic hydrophilic block A in the diblock polymers A-B of the invention is preferably greater than 60%, and more particularly greater than 70%.

The proportion by mass of the ionic hydrophilic block A in the triblock polymers B-A-B of the invention is preferably greater than 50%, and more particularly greater than 60%.

In addition, in a preferred embodiment of the invention, the diblock or triblock polymers used according to the invention as gelling agents have ionic water-soluble polymeric blocks A which are completely water-soluble, that is to say completely free of hydrophobic monomer, and hydrophobic polymeric blocks B which are completely hydrophobic, that is to say completely free of hydrophilic monomer.

The preferred diblock or triblock polymers, containing ionic polymeric blocks A which are completely water-soluble and polymeric blocks B which are completely hydrophobic, have the advantage of being easy to synthesize and of giving equally good gelling as the others for lower concentrations.

Among the particularly preferred diblock polymers, there may be mentioned the polystyrene/sodium polyacrylate diblocks and more particularly:

the polystyrene (2000 g/mol)-sodium polyacrylate (11500 g/mol) diblock polymer where the water-soluble ionic block (sodium polyacrylate) represents 85.2% of the total weight of the diblock polymer;

the polystyrene (1800 g/mol)-sodium polyacrylate (42450 g/mol) diblock polymer where the water-soluble ionic block (sodium polyacrylate) represents 95.9% of the total weight of the diblock polymer;

the polystyrene (4300 g/mol)-sodium polyacrylate (25460 g/mol) diblock polymer where the water-soluble ionic block represents 85.55% of the total weight of the diblock copolymer.

Among the particularly preferred triblock polymers, there may be mentioned the polystyrene/sodium polyacrylate/polystyrene triblock polymers and more particularly:

the polystyrene (2500 g/mol)-sodium polyacrylate (29800 g/mol)-polystyrene (2500 g/mol) triblock copolymer where the quantity of water-soluble block represents 85.63% of the total weight of the triblock copolymer.

The polymers of the invention may be prepared by the methods of synthesis conventionally used for obtaining block polymers. There may be mentioned living polymerization of the anionic or cationic type, and controlled free-radical polymerization which may be carried out according to various methods such as for example atom transfer radical polymerization (ATRP), free-radical methods such as nitroxides or alternatively radical addition-fragmentation chain transfer such as the MADIX (Macromolecular Design via Interchange of Xanthate) method. These methods of synthesis may be used to obtain the blocks A and B of the polymers of the invention; they may also be used to synthesize only one of the two blocks of the polymer of the invention, the other block being introduced into the final polymer by means of the initiator used or alternatively by a coupling reaction between the blocks A and B.

The concentration by mass of the polymer in the composition preferably varies from 0.01% to 30% by weight, preferably between 0.1% and 20% by weight relative to the total weight of the composition.

The 4,4-diarylbutadiene compounds in accordance with the invention are preferably chosen from those corresponding to the following formula (II):

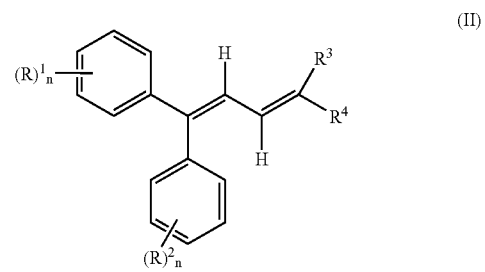

(II)

in which the diene system is of the Z,Z; Z,E; E,Z or E,E configuration or mixtures of the said configurations, and wherein $R^1$ and $R^2$, which may be identical or different, are each hydrogen, a $C_1$-$C_{20}$ alkyl radical, a $C_2$-$C_{10}$ alkenyl radical, a $C_1$-$C_2$ alkoxy radical, a $C_3$-$C_{10}$ cycloalkyl radical, a $C_3$-$C_{10}$ cycloalkenyl radical, a $C_1$-$C_{20}$ alkoxycarbonyl radical, a $C_1$-$C_{12}$ monoalkylamino radical, a $C_1$-$C_{12}$ dialkylamino radical, an aryl radical, a heteroaryl radical or a water-solubilizing substituent selected from among a carboxylate residue, a sulfonate residue or an ammonium residue; $R^3$ is a group $COOR^5$, $COR^5$, $CONR^5R^6$, CN, $O=S(-R^5)=O$, $O=S(-OR^5)=O$, $R^7O-P-(-OR^8)=O$, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$C_{18}$ aryl radical, an optionally substituted $C_3$-$C_7$ heteroaryl radical; $R^4$ is a group $COOR^6$, $COR^6$, $CONR^5R^6$, CN, $O=S(-R^6)=O$, $O=S(-OR^6)=O$, $R^7O-P-(-OR^8)=O$, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$C_{18}$ aryl radical, an optionally substituted $C_3$-$C_7$ heteroaryl radical; the radicals $R^5$ to $R^8$, which may be identical or different, are each hydrogen, a $C_1$-$C_{20}$ alkyl radical, a $C_2$-$C_{10}$ alkenyl radical, $C_3$-$C_{10}$ cycloalkyl radical, a $C_7$-$C_{10}$ bicycloalkyl radical, a $C_3$-$C_{10}$ bicycloalkenyl radical, a $C_7$-$C_{10}$ cycloalkenyl radical, an optionally substituted aryl radical, an optionally substituted heteroaryl radical; and n ranges from 1 to 3; with the proviso that the radicals $R^3$ to $R^8$ can together form, with the carbon atoms from which they depend, a $C_5$-$C_6$ ring which may be fused.

As $C_1$-$C_{20}$ alkyl radicals, there may be mentioned, for example: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbuty, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

As $C_2$-$C_{10}$ alkenyl groups, there may be mentioned, for example: ethenyl, n-propenyl, 1-methylethenyl, n-butenyl, 1-methylpropenyl, 2-methylpropenyl, 1,1-dimethylethenyl, n-pentenyl, 1-methylbutenyl, 2-methylbutenyl, 3-methylbutenyl, 2,2-dimethylpropenyl, 1-ethylpropenyl, n-hexenyl, 1,1-dimethylpropenyl, 1,2-dimethylpropenyl, 1-methylpentenyl, 2-methylpentenyl, 3-methylpentenyl, 4-methylpentenyl, 1,1-dimethylbutenyl, 1,2-dimethylbutenyl, 1,3-dimethylbutenyl, 2,2-dimethylbutenyl, 2,3-dimethylbutenyl, 3,3-dimethylbutenyl, 1-ethylbutenyl, 2-ethylbutenyl, 1,1,2-trimethylpropenyl, 1,2,2-trimethylpropenyl, 1-ethyl-1-methylpropenyl, 1-ethyl-2-methylpropenyl, n-heptenyl, n-octenyl, n-nonenyl, n-decenyl.

As $C_1$-$C_{12}$ alkoxy radicals, there may be mentioned: methoxy, n-propxy, 1-methylpropoxy, 1-methylethoxy, n-pentoxy, 3-methylbutoxy, 2,2-dimethylpropoxy, 1-methyl-1-ethylpropoxy, octoxy, ethoxy, n-propoxy, n-butoxy, 2-methylpropoxy, 1,1-dimethylpropoxy, hexoxy, heptoxy, 2-ethylhexoxy.

As $C_1$-$C_{20}$ alkoxycarbonyl radicals, there may be mentioned esters of $C_1$-$C_{20}$ alcohols.

As $C_1$-$C_{12}$ monoalkylamino or dialkylamino radicals, there may be mentioned those in which the alkyl radical(s) is(are) selected from among methyl, n-propyl, 2-methylpropyl, 1,1-dimethylethyl, hexyl, heptyl, 2-ethylhexyl, isopropyl, 1-methylpropyl, n-pentyl, 3-methylbutyl, 2,2-dimethylpropyl, 1-methyl-1-ethylpropyl, octyl.

As $C_3$-$C_{10}$ cycloalkyl radicals, there may be mentioned, for example: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

As $C_3$-$C_{10}$ cycloalkenyl radicals having one or more double bonds, there may be mentioned: cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctetraenyl, cyclononenyl or cyclodecenyl.

The cycloalkyl or cycloalkenyl radicals may comprise one or more substituents (preferably from 1 to 3) selected, for example, from among halogens such as chlorine, fluorine or bromine; cyano; nitro; amino; $C_1$-$C_4$ alkylamino; $C_1$-$C_4$ dialkylamino; $C_1$-$C_4$ alkyl; $C_1$-$C_4$ alkoxy; hydroxyl; they may also comprise from 1 to 3 heteroatoms such as sulfur, oxygen or nitrogen whose free valencies may be saturated with a hydrogen or a $C_1$-$C_4$ alkyl radical.

The bicycloalkyl or bicycloalkenyl groups are selected, for example, from among bicyclic terpenes such as pinane, borane, pinene or camphor or adamantane derivatives.

The aryl groups are preferably selected from among phenyl or naphthyl rings, which may comprise one or more substituents (preferably from 1 to 3) chosen for example from halogen such as chlorine, fluorine or bromine; cyano; nitro; amino; $C_1$-$C_4$ alkylamino; $C_1$-$C_4$ dialkylamino; $C_1$-$C_4$ alkyl; $C_1$-$C_4$ alkoxy; hydroxyl. Phenyl, methoxyphenyl, naphthyl and thienyl are more particularly preferred.

The heteroaryl groups comprise in general one or more heteroatoms selected from among sulfur, oxygen or nitrogen.

The water-solubilizing groups are for example carboxyl and sulfoxy residues, and more particular their salts with physiologically acceptable cations such as alkali metal salts or trialkylammonium salts such as tri(hydroxyalkyl)ammonium or 2-methylpropan-1-ol-2-ammonium salts. There may also be mentioned ammonium groups such as alkylammoniums and their salified forms with physiologically acceptable anions.

The compounds of formula (II) are known per se and their structures and their syntheses are described in DE-1-9-755, 649, EP-916,335, EP-1-133,980 and EP-1,133,981.

By way of examples of compounds of formula (II), the following are representative:

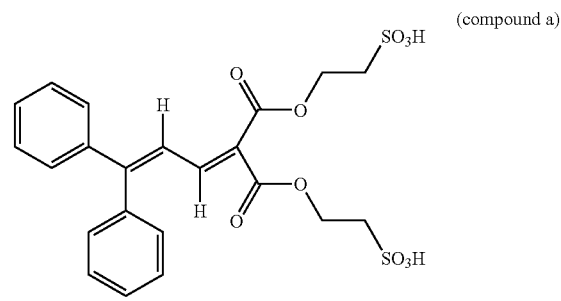
(compound a)

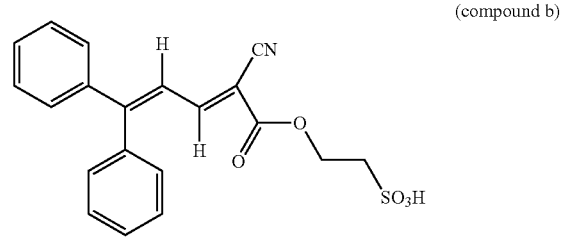
(compound b)

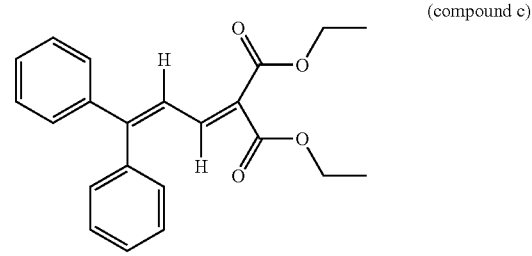
(compound c)

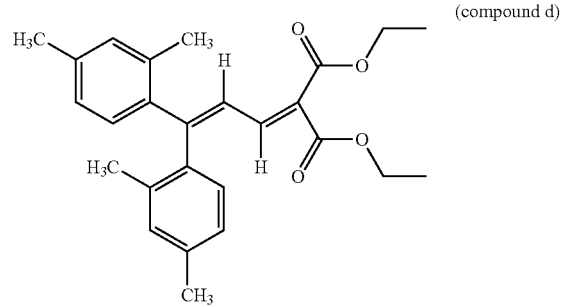
(compound d)

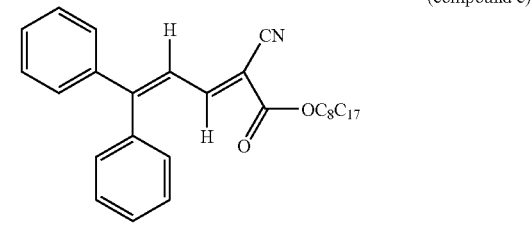
(compound e)

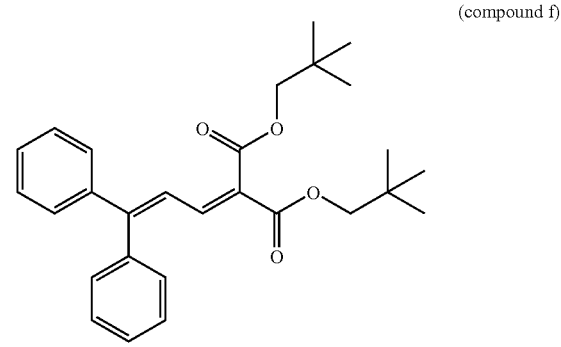
(compound f)

The preferred compounds of formula (II) are those in which:

n=1 or 2;

$R^1$ and $R^2$, which maybe identical or different, are each hydrogen, a $C_1$-$C_{20}$ alkyl radical, a $C_1$-$C_{12}$ alkoxy radical, a $C_1$-$C_{12}$ monoalkylamino radical, a $C_1$-$C_{12}$ dialkylamino radical, a water-solubilizing substituent selected from a carboxylate group, a sulfonate group or an ammonium residue;

$R^3$ is a group $COOR^5$, $COR^5$, $CONR^5R^6$, a $C_1$-$C_{20}$ alkyl radical, a $C_3$-$C_{10}$ cycloalkyl radical, a $C_3$-$C_{10}$ cycloalkenyl radical, a $C_7$-$C_{10}$ bicycloalkyl radical, optionally substituted phenyl, naphthyl or thienyl;

$R^4$ is a group $COOR^6$, $COR^6$, $CONR^5R^6$, a $C_1$-$C_{20}$ alkyl radical, a $C_3$-$C_6$ cycloalkyl radical, a $C_3$-$C_{10}$ cycloalkenyl radical, a $C_7$-$C_{10}$ bicycloalkyl radical, optionally substituted phenyl, naphthyl or thienyl;

the radicals $R^5$ and $R^6$, which may be identical or different, are each hydrogen, a $C_1$-$C_{12}$ alkyl radical, a $C_3$-$C_{10}$ cycloalkyl radical, a $C_3$-$C_{10}$ cycloalkenyl radical, a $C_7$-$C_{10}$ bicycloalkyl radical, a $C_3$-$C_{10}$ bicycloalkenyl radical, optionally substituted phenyl or naphthyl.

Among these compounds, there are more particularly preferred those for which:

$R^1$ and $R^2$, which may be identical or different, are each hydrogen, a $C_1$-$C_{20}$ alkyl radical, a $C_1$-$C_{20}$ alkoxy radical, a water-solubilizing substituent selected from among a carboxylate group, a sulfonate group or an ammonium residue;

$R^3$ is a group $COOR^5$, $COR^5$, $CONR^5R^6$;

$R^4$ is a group $COOR^6$, $COR^6$, $CONR^5R^6$;

the radicals $R^5$ and $R^6$, which may be identical or different, are each hydrogen, a $C_1$-$C_{12}$ alkyl radical, a $C_3$-$C_6$ cycloalkyl radical, a $C_3$-$C_{10}$ cycloalkenyl radical, a $C_7$-$C_{10}$ bicycloalkyl radical, a $C_3$-$C_{10}$ bicycloalkenyl radical, optionally substituted phenyl or naphthyl.

According to a particularly preferred embodiment, the compounds of formula (II) are chosen from those of the following formula (II'):

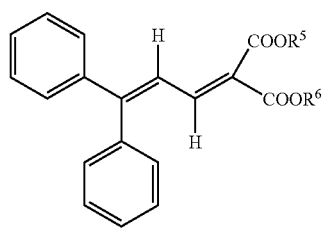

(II')

wherein the radicals $R^5$ and $R^6$, which maybe identical or different, are each hydrogen, a $C_1$-$C_{20}$ alkyl radical, a $C_3$-$C_6$ cycloalkyl radical, a $C_3$-$C_{10}$ cycloalkenyl radical.

Among these compounds of formula (II'), there may be mentioned, more particularly, 1,1-dicarboxy(2,2'-dimethylpropyl)-4,4-diphenylbutadiene having the structure:

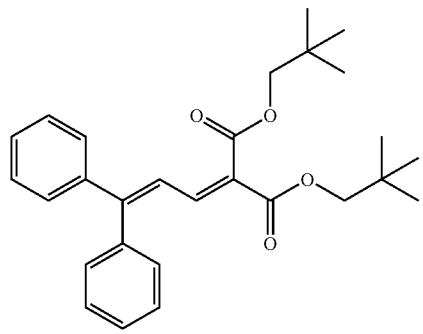

(compound f)

Another 4,4-diarylbutadiene family which may be used in the emulsions according to the invention, are those corresponding to the following formula (III):

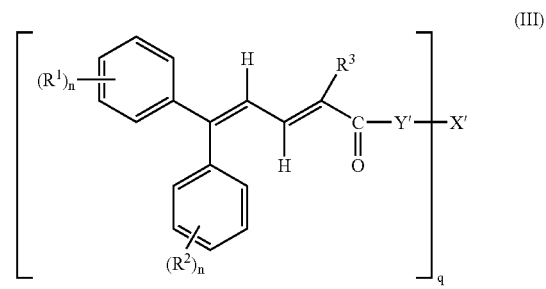

(III)

in which the diene system is of the Z,Z; Z,E; E,Z or E,E configuration or mixtures of the said configurations and wherein:

$R^1$, $R^2$, $R^3$ and $\underline{n}$ have the meanings indicated in the preceding formula (I);

Y' is a group —O— or —$NR^9$—;

$R^9$ is hydrogen, a linear or branched $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an aryl radical, a heteroaryl radical;

X' is a residue of a linear or branched, aliphatic or cycloaliphatic polyol comprising from 2 to 10 hydroxyl groups and having the valency q; with the proviso that the carbon chain of the said residue may be interrupted by one or more sulfur or oxygen atoms, one or more imine groups, one or more $C_1$-$C_4$ alkylimino groups;

q ranges from 2 to 10;

X' is $C_2$-$C_{20}$ a polyol residue comprising from 2 to 10 hydroxyl groups, and in particular:

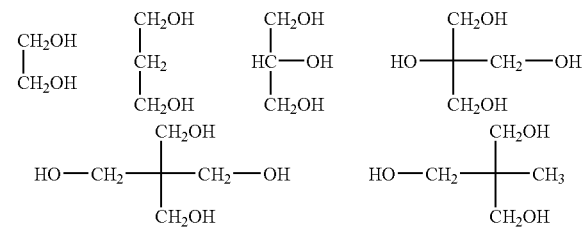

-continued

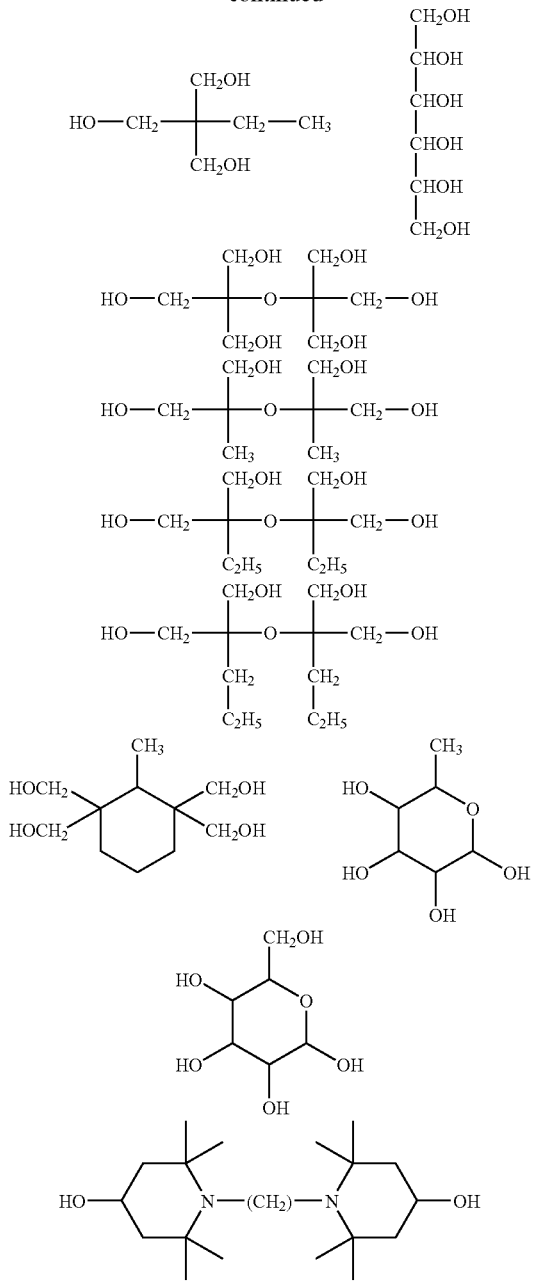

The more preferred compounds of formula (III) are those for which:
$R^1$ and $R^2$, which may be identical or different, are each hydrogen, a $C_1$-$C_{12}$ alkyl radical, a $C_1$-$C_8$ alkoxy radical, a water-solubilizing substituent selected from among a carboxylate group, a sulfonate group or an ammonium residue;
$R^3$ is a group $COOR^5$, $CONR^5R^6$, CN, a $C_3$-$C_{10}$ cycloalkyl radical, a $C_7$-$C_{10}$ bicycloalkyl radical;
$R^5$ and $R^6$, which may be identical or different, are each a linear or branched $C_1$-$C_{20}$ alkyl radical, a $C_3$-$C_{10}$ cycloalkyl radical, a $C_7$-$C_{10}$ bicycloalkyl radical, optionally substituted naphthyl or phenyl;
X' is a $C_2$-$C_{20}$ polyol residue comprising from 2 to 6 hydroxyl groups and more particularly from 2 to 4.

The still more preferred compounds of formula (III) are those for which:
X' is an ethanol or pentaerythritol residue.
The even more particularly preferred compounds of formula (III) are selected from among:

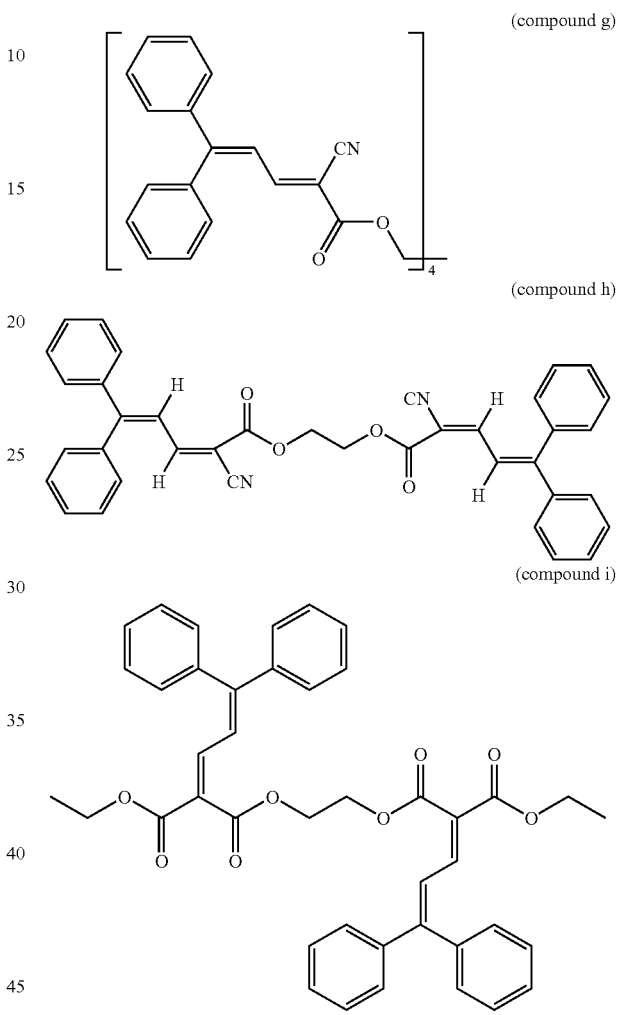

The compounds of formula (III) as defined above are known per se and their structures and their syntheses are described in EP-A-1-008,586.

The 4,4-diarylbutadiene compounds are preferably present in the compositions in proportions ranging from 0.1% to 20% by weight, more preferably from 1% to 10% by weight relative to the total weight of the composition.

The compositions according to the invention may be provided in any of the galenic forms containing an aqueous phase, which are conventionally used for topical application, and in particular in the form of a lotion or a serum with no fatty phase, of dispersions of the emulsion type having a liquid or semiliquid consistency of the milk type, which are obtained by dispersing a fatty phase in an aqueous phase (O/W) or conversely (W/O), or suspensions or emulsions having a soft, semisolid or solid consistency of the cream or gel type, or of multiple emulsions (W/O/W or O/W/O), microemulsions, vesicular dispersions of the ionic and/or nonionic type, or wax/aqueous phase dispersions. These compositions are prepared according to the customary methods.

According to a particular embodiment of the invention, the oil-in-water or water-in-oil emulsions prepared with the diblock or triblock polymers according to the invention may contain only 1% by weight or less, and may even be free of emulsifying surfactants, while being stable during storage.

The nature of the fatty phase that may enter into the composition of the emulsion type according to the invention is not critical and it may thus comprise all the compounds which are already known in general as being suitable for the manufacture of oil-in-water type emulsions. In particular, these compounds may be chosen, alone or as mixtures, from various fatty substances, oils of plant, animal or mineral origin, natural or synthetic waxes, and the like.

Among the oils which may comprise the composition of the fatty phase, there may be mentioned in particular:
mineral oils such as paraffin oil and liquid paraffin,
oils of animal origin, such as perhydrosqualene,
oils of plant origin, such as sweet almond oil, avocado oil, castor oil, olive oil, jojoba oil, sesame oil, groundnut oil, grape seed oil, rapeseed oil, copra oil, hazelnut oil, shea butter, palm oil, apricot kernel oil, calophyllum oil, rice bran oil, maize germ oil, wheat germ oil, soya bean oil, sunflower oil, evening primrose oil, sunflower oil, passion flower oil and rye oil,
synthetic oils, for example esters such as purcellin oil, butyl myristate, isopropyl myristate, cetyl myristate, isopropyl palmitate, isopropyl adipate, ethylhexyl adipate, butyl stearate, hexyldecyl stearate, isopropyl stearate, octyl stearate, isocetyl stearate, decyl oleate, hexyl laurate, propylene glycol dicaprylate and esters derived from lanolic acid such as isopropyl lanolate, isocetyl lanolate, isoparaffins and poly-α-olefins.

As other oils which can be used in the emulsions according to the invention, there may also be mentioned C12-C15 fatty alcohol benzoates (Finsolv TN from FINETEX), ethers, lipophilic amino acid derivatives such as isopropyl N-lauroylsarcosinate (Eldew SL-205 from Ajinomoto), fatty alcohols such as lauryl, cetyl, myristyl, stearyl, palmityl or oleyl alcohol and 2-octyldodecanol, acetylglycerides, octanoates and decanoates of alcohols and polyalcohols such as those of glycol and of glycerol, ricinoleates of alcohols and polyalcohols such as those of cetyl, fatty acid triglycerides such as caprylic/capric triglycerides, C10-C18 saturated fatty acid triglycerides, fluorinated and perfluorinated oils, lanolin, hydrogenated lanolin, acetylated lanolin and finally volatile or nonvolatile silicone oils.

Of course, the fatty phase may also contain one or more conventional lipophilic cosmetic adjuvants, such as for example waxes, lipophilic gelling agents, surfactants, organic or mineral particles, and in particular those which are already customarily used in the manufacture and production of anti-sun cosmetic compositions.

Conventionally, the aqueous phase may consist of water, or a mixture of water and polyhydric alcohol(s) such as for example glycerol, propylene glycol, butylene glycol and sorbitol, or alternatively a mixture of water and water-soluble lower alcohol(s) such as ethanol, isopropanol or butanol (aqueous-alcoholic solution).

The compositions in accordance with the invention may further comprise other additional organic or inorganic UV-screening agents which are active in UV-A and/or UV-B regions, which are water-soluble or fat-soluble or alternatively insoluble in the commonly-used cosmetic solvents.

The additional organic screening agents are selected in particular from among anthranilates; cinnamic derivatives; dibenzoylmethane derivatives; salicylic derivatives, camphor derivatives; triazine derivatives such as those described in U.S. Pat. No. 4,367,390, EP-863,145, EP-517,104, EP-570,838, EP-796,851, EP-775,698, EP-878,469 and EP-933,376; benzophenone derivatives, in particular those described in EP-A-1-046,391 and DE-1-0,012,408; β, β'-diphenyl acrylate derivatives, benzotriazole derivatives, benzimidazole derivatives; imidazolines; bis-benzoazolyl derivatives as described in EP-669,323 and U.S. Pat. No. 2,463,264; p-aminobenzoic acid (PABA) derivatives; methylenebis(hydroxyphenylbenzotriazole) derivatives as described in U.S. Pat. Nos. 5,237,071, 5,166,355, GB-2,303, 549, DE-1-9,726,184 and EP-893,119; screening polymers and screening silicones such as those described in WO 93/04665; dimers derived from (x-alkylstyrene such as those described in DE-1-9-855,649 and mixtures thereof.

As examples of organic screening agents which are active in the UV-A and/or UV-B regions, there may be mentioned those designated below under their INCI name:
para-Aminobenzoic acid derivatives:
PABA,
Ethyl PABA,
Ethyl Dihydroxypropyl PABA,
Ethylhexyl Dimethyl PABA sold in particular under the name "ESCALOL 507" by ISP,
Glyceryl PABA,
PEG-25 PABA sold under the name "UVINUL P25" by BASF,
Salicylic derivatives:
Homosalate sold under the name "Eusolex HMS" by Rona/EM Industries,
Ethylhexyl Salicylate sold under the name "NEO HELIOPAN OS" by Haarmann and REIMER,
Dipropyleneglycol Salicylate sold under the name "DIPSAL" by SCHER,
TEA Salicylate, sold under the name "NEO HELIOPAN TS" by Haarmann and REIMER,
Dibenzoylmethane derivatives:
Butyl Methoxydibenzoylmethane sold in particular under the trademark "PARSOL 1789" by HOFFMANN LA ROCHE, Isopropyl Dibenzoylmethane,
Cinnamic derivatives:
Ethylhexyl Methoxycinnamate sold in particular under the trademark "PARSOL MCX" by HOFFMANN LA ROCHE,
Isopropyl Methoxy cinnamate,
Isoamyl Methoxy cinnamate sold under the trademark "NEO HELIOPAN E 1000" by HAARMANN and REIMER,
Cinoxate,
DEA Methoxycinnamate,
-Diisopropyl Methylcinnamate,
Glyceryl Ethylhexanoate Dimethoxycinnamate,
β,β'-Diphenyl acrylate derivatives:
Octocrylene sold in particular under the trademark "UVINUL N539" by BASF,
Etocrylene, sold in particular under the trademark "UVINUL N35" by BASF,
Benzophenone derivatives:
Benzophenone-1 sold under the trademark "UVINUL 400" by BASF,
Benzophenone-2 sold under the trademark "UVINUL D50" by BASF,
Benzophenone-3 or Oxybenzone, sold under the trademark "UVINUL M40" by BASF, Benzophenone-4 sold under the trademark "UVINUL MS40" by BASF,
Benzophenone-5,
Benzophenone-6 sold under the trademark "Helisorb 11" by Norquay,
Benzophenone-8 sold under the trademark "Spectra SOrb UV-24" by American Cyanamid,
Benzophenone-9 sold under the trademark "UVINUL DS-49" by BASF,
Benzophenone-12,
n-Hexyl 2-(4-diethylamino-2-hydroxybenzoyl)benzoate,
Benzylidenecamphor derivatives:
3-Benzylidene camphor manufactured under the name "MEXORYL SD" by CHIMEX,
4-Methylbenzylidene camphor sold under the name "EUSO-LEX 6300" by MERCK,
Benzylidene Camphor Sulfonic Acid manufactured under the name "MEXORYL SL" by CHIMEX,
Camphor Benzalkonium Methosulfate manufactured under the name "MEXORYL SO" by CHIMEX,
Terephthalylidene Dicamphor Sulfonic Acid manufactured under the name "MEXORYL SX" by CHIMEX,
Polyacrylamidomethyl Benzylidene Camphor manufactured under the name "MEXORYL SW" by CHIMEX,
Phenylbenzimidazole derivatives:
Phenylbenzimidazole Sulfonic Acid sold in particular under the trademark "EUSOLEX 232" by MERCK,
Disodium Phenyl Dibenzimidazole Tetra-sulfonate sold under the trademark "NEO HELIOPAN AP" by Haarmann and REIMER,
Triazine derivatives:
Anisotriazine sold under the trademark "TINOSORB S" by CIBA GEIGY,
Ethylhexyl triazone sold in particular under the trademark "UVINUL T150" by BASF,
2,4,6-Tris(diisobutyl 4'-aminobenzalmalonate)-s-triazine,
Diethylhexyl Butamido Triazone sold under the trademark "UVASORB HEB" by SIGMA 3V,
Phenylbenzotriazole derivatives:
Drometrizole Trisiloxane sold under the name "Silatrizole" by RHODIA CHIMIE,
Methylene bis-Benzotriazolyl Tetramethylbutylphenol, sold in solid form under the trademark "MIXXIM BB/100" by FAIRMOUNT CHEMICAL or in micronized form in aqueous dispersion under the trademark "TINOSORB M" by CIBA SPECIALTY CHEMICALS,
Anthranilic derivatives:
Menthyl anthranilate sold under the trademark "NEO HELIOPAN MA" by Haarmann and REIMER,
Imidazoline derivatives:
Ethylhexyl Dimethoxybenzylidene Dioxoimidazoline Propionate,
Benzalmalonate derivatives:
Polyorganosiloxane with benzalmalonate functional groups sold under the trademark "PARSOL SLX" by HOFFMANN LA ROCHE
Benzoxazole derivatives:
2,4-Bis[5-1-(dimethylpropyl)benzoxazol-2-yl-(4-phenyl) imino]-6-(2-ethylhexyl)imino-1,3,5-triazine sold under the name Uvasorb K2A by Sigma 3V; and mixtures thereof.
The additional organic UV-screening agents which are more particularly preferred are chosen from the following compounds:
Ethylhexyl Salicylate,
Butyl Methoxydibenzoylmethane,
Ethylhexyl Methoxycinnamate,
Octocrylene,
Phenylbenzimidazole Sulfonic Acid,
Terephthalylidene Dicamphor Sulfonic,
Benzophenone-3,
Benzophenone-4,
Benzophenone-5,
n-Hexyl 2-(4-diethylamino-2-hydroxybenzoyl)benzoate,
4-Methylbenzylidene camphor,
Disodium Phenyl Dibenzimidazole Tetra-sulfonate,
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone 15,
2,4-Bis-[5-1-(dimethylpropyl)benzoxazol-2-yl-(4-phenyl) imino]-6-(2-ethylhexyl)imino-1,3,5-triazine and mixtures thereof.

The additional inorganic screening agents are selected from among pigments or nanopigments (average size of the primary particles: generally between 5 nm and 100 nm, preferably between 10 nm and 50 nm) of metal oxides, coated or uncoated, such as for example nanopigments of titanium oxide (amorphous or crystallized in rutile and/or anatase form), iron oxide, zinc oxide, zirconium oxide or cerium oxide which are all UV photoprotective agents well known per se. Conventional coating agents are moreover alumina and/or aluminium stearate. Such nanopigments of metal oxides, coated or uncoated, are in particular described in EP-518,772 and EP-518,773.

The additional screening agents according to the invention are generally present in the compositions according to the invention in an amount ranging from 0.1% to 30% by weight, and preferably from 0.5% to 15% by weight, relative to the total weight of the composition.

The compositions according to the invention may also contain agents for artificially bronzing and/or tanning the skin (self-tanning agents).

The self-tanning agents are generally chosen from mono- or polycarbonylated compounds such as for example isatin, alloxan, ninhydrin, glyceraldehydes, mesotartaric aldehyde, glutaraldehyde, erythrulose, derivatives of 4,5-pyrazolindiones as described in FR-2-466,492 and WO 97/35842, dihydroxyacetone (DHA), 4,4-dihydroxypyrazolin-5-one derivatives as described in EP-903,342. DHA will preferably be used.

DHA may be used in free form and/or encapsulated for example into lipid vesicles such as liposomes, which are described in particular in WO 97/25970.

The mono- or polycarbonylated self-tanning agents are generally present in the compositions according to the invention in proportions ranging from 0.1% to 10% by weight relative to the total weight of the composition, and preferably from 0.2% to 8% by weight relative to the total weight of the composition.

The compositions in accordance with the present invention may additionally comprise conventional cosmetic adjuvants, selected in particular from among organic solvents, ionic or nonionic thickeners, demulcents, humectants, opacifying agents, stabilizers, emollients, silicones, insect repellents, perfumes, preservatives, surfactants, fillers, active agents, pigments, polymers, propellants, alkalinizing or acidifying agents or any other ingredient customarily used in the cosmetic and/or dermatological field.

Of course, persons skilled in the art will be careful to choose the possible additional compound(s) cited above and/or their quantities such that the advantageous properties intrinsically attached to the compositions in accordance with the invention are not, or not substantially, impaired by the addition(s) envisaged.

Among the organic solvents lower alcohols and polyols may be mentioned.

Among the thickeners, there may be mentioned crosslinked acrylic polymers such as the Carbomers provided by Noveon, acrylate/C10-30 alkyl acrylate crosslinked polymers of the Pemulen type provided by Noveon or polyacrylate-3 sold under the name Viscophobe DB 1000 by Amerchol); polymers derived from acrylamido-2-methyl-propanesulfonic acid (Hostacerin AMPS provided by Clariant, Sepigel 305 provided by Seppic), synthetic neutral polymers such as poly-N-vinylpyrrolidone, polysaccharides such as guar and xanthan gums, and modified or unmodified cellulose derivatives such as hydroxypropylated guar gum, methylhydroxyethylcellulose and hydroxypropylmethylcellulose.

The compositions according to the invention find application in a large number of treatments, in particular cosmetic treatments, of the skin, the lips and the hair, including the scalp, in particular for the production and/or care of the skin, the lips and/or the hair, and/or for making up the skin and/or the lips.

The present invention thus features the use of the subject compositions for the manufacture of products for the cosmetic treatment of the skin, the lips and the hair, including the scalp, in particular for the protection and/or care of the skin, the lips and/or the hair, and/or for making up the skin and/or the lips.

The cosmetic compositions according to the invention may, for example, be used as care and/or sun protection product for the face and/or the body having a liquid to semiliquid consistency, such as milks, creams which are more or less unctuous, gel creams or pastes. They may be optionally packaged as an aerosol and may be provided in the form of a mousse or a spray.

The compositions according to the invention in the form of vaporizable fluid lotions in accordance with the invention are applied to the skin or the hair in the form of fine particles by means of pressurized devices. The devices in accordance with the invention are well known to those skilled in the art and comprise nonaerosol pumps or "atomisers", the aerosol containers comprising a propellant and aerosol pumps using compressed air as propellant. The latter are described in U.S. Pat. Nos. 4,077,441 and 4,850,517.

The compositions packaged as an aerosol in accordance with the invention contain in general conventional propellants such as for example the hydrofluorinated compounds dichlorodifluoromethane, difluoroethane, dimethyl ether, isobutene, n-butane, propane, trichlorofluoromethane. They are preferably present in quantities ranging from 15 to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Photoprotective Milks (Surfactant-Free Emulsions Stabilized with a Diblock Copolymer A-B)

| Ingredients | Emulsion 1 (not in accordance with the invention) | Emulsion 2 |
|---|---|---|
| Octyl methoxycinnamate | 7 | 7 |
| 1,1-dicarboxy-(2'2'-dimethylpropyl)-4,4-diphenylbutadiene (Compound f) | 0 | 5 |
| Alkyl $C_{12-15}$ benzoate | 10 | 10 |
| Glycerin | 3 | 3 |
| 3,3'-terephthalylidene-10,10'-dicamphorsulfonic acid | 5 | 0 |
| Polystyrene (2000 g/mol)-sodium polyacrylate (11500 g/mol) diblock polymer | 3 | 3 |
| Triethanolamine | 2.3 | 0 |
| Preservative | 0.3 | 0.3 |
| Water | qs 100 | qs |

The emulsions 1 and 2 have equivalent photoprotective properties.

The emulsion 1 becomes very fluid and exhibits a phenomena of creaming after 7 days at room temperature.

The emulsion 2 according to the invention remains stable after 7 days and has a nice texture of the cream type.

Mode of Preparation of the Emulsions:

The block copolymer is solubilized for 2 hours with stirring in the aqueous phase at 60° C.; the solution obtained is macroscopically homogeneous. Each emulsion is prepared by slowly introducing the oily phase into the aqueous phase with stirring with the aid of a Moritz-type homogenizer at a stirring speed of 2000 rpm for 15 minutes.

Example 2

Photoprotective Milks (Surfactant-Free Emulsions Stabilized with a Triblock Copolymer B-A-B)

| Ingredients | Emulsion 3 (not in accordance with the invention) | Emulsion 4 |
|---|---|---|
| Octyl methoxycinnamate | 7 | 7 |
| 1,1-dicarboxy-(2'2'-dimethylpropyl)-4,4-diphenylbutadiene (Compound f) | 0 | 5 |
| Alkyl $C_{12-15}$ benzoate | 10 | 10 |
| Glycerin | 3 | 3 |
| 3,3'-terephthalylidene-10,10'-dicamphorsulfonic acid | 5 | 0 |
| Polystyrene (2500 g/mol)-sodium polyacrylate (29800 g/mol)-polystyrene (2500 g/mol) triblock polymer | 0.6 | 0.6 |
| Triethanolamine | 2.3 | 0 |
| Preservative | 0.3 | 0.3 |
| Water | qs 100 | qs 100 |

The emulsions 3 and 4 have equivalent photoprotective properties.

The emulsion 3 becomes fluid and becomes macroscopically destabilized after 24 hours, with the appearance of a phenomena of creaming.

The emulsion 4 according to the invention remains stable after 24 hours and has a nice texture of the cream type.

Mode of Preparation of the Emulsions:

The block copolymer is solubilized for 2 hours with stirring in the aqueous phase at 60° C.; the solution obtained is macroscopically homogeneous. Each emulsion is prepared by slowly introducing the oily phase into the aqueous phase with stirring with the aid of a Moritz-type homogenizer at a stirring speed of 2000 rpm for 15 minutes.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective composition comprising at least one aqueous phase, at least one water-soluble or water-dispersible polymer having a diblock structure A-B or a triblock structure B-A-B wherein A is an ionic water-soluble polymeric block and B is a hydrophobic polymeric block and at least one system screening out UV radiation, said at least one screening system comprising at least one 4,4-diarylbutadiene UV-A screening agent.

2. The photoprotective composition as defined by claim 1, said ionic water-soluble block A comprising the polymerizate of one or more water-soluble monomers (Ia) or salts thereof, selected from among:
   (meth)acrylic acid,
   styrenesulfonic acid,
   vinylsulfonic acid and (meth)allylsulfonic acid,
   vinylphosphonic acid,
   maleic acid,
   itaconic acid,
   crotonic acid,
   dimethyldiallylammonium chloride,
   methylvinylimidazolium chloride,
   ethylenic carboxybetaines or sulfobetaines produced by quaternization of ethylenically unsaturated monomers containing an amine functional group, with sodium salts of a carboxylic acid having an active halogen or with cyclic sulfones,
   water-soluble vinyl monomers of the following formula (A):

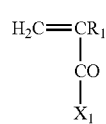

in which $R_1$ is H, $-CH_3$, $-C_2H_5$ or $-C_3H_7$ and $X_1$ is selected from among:
(i) alkyl oxides of the $-OR_2$ type wherein $R_2$ is a saturated or unsaturated, linear or branched hydrocarbon radical having from 1 to 6 carbon atoms, substituted with at least one sulfonic ($-SO_3^-$) and/or sulfate ($-SO_4^-$) and/or phosphate ($-PO_4H_2^-$) and/or quaternary ammonium ($-N^+R_3R_4R_5$) group in which $R_3$, $R_4$ and $R_5$, which may be identical or different, are each a saturated or unsaturated, linear or branched hydrocarbon radical having 1 to 6 carbon atoms, provided that the sum of the carbon atoms of $R_2+R_3+R_4+R_5$ does not exceed 6; the radical $R_2$ is optionally substituted with a halogen atom (iodine, bromine, chlorine, fluorine); hydroxyl ($-OH$); ether ($-O-$); primary amine ($-NH_2$); secondary amine ($-NHR_6$) and/or tertiary amine ($-NR_6R_7$) in which $R_6$ and $R_7$; which may be identical or different, are each a saturated or unsaturated, linear or branched hydrocarbon radical having 1 to 6 carbon atoms, provided that the sum of the carbon atoms of $R_2+R_6+R_7$ does not exceed 6; and (ii) $-NH_2$, $-NHR_8$ and $-NR_8R_9$ groups in which $R_8$ and $R_9$, which may be identical or different, are each a saturated or unsaturated, linear or branched hydrocarbon radical having 1 to 6 carbon atoms, provided that the total number of carbon atoms of $R_8+R_9$ does not exceed 6, said $R_8$ and/or $R_9$ being substituted with at least one sulfonic ($-SO_3^-$) and/or sulfate ($-SO_4^-$) and/or phosphate ($-PO_4H_2^-$) and/or quaternary amine ($-N^+R_{10}R_{11}R_{12}$) group in which $R_{10}$, $R_{11}$ and $R_{12}$, which may be identical or different, are each a saturated or unsaturated, linear or branched hydrocarbon radical having 1 to 6 carbon atoms, provided that the sum of the carbon atoms of $R_8+R_9+R_{10}+R_{11}+R_{12}$ does not exceed 6; the radicals $R_8$ and/or $R_9$ are optionally substituted with a halogen atom (iodine, bromine, chlorine, fluorine); a hydroxyl group ($-OH$); an ether group ($-O-$); a primary amine group ($-NH_2$); a secondary amine group ($-NHR_{13}$) and/or a tertiary amine group ($-NR_{13}R_{14}$) in which $R_{13}$ and $R_{14}$, which may be identical or different, are each a saturated or unsaturated, linear or branched hydrocarbon radical having 1 to 6 carbon atoms, provided that the sum of the carbon atoms of $R_8+R_9+R_{13}+R_{14}$ does not exceed 6.

3. The photoprotective composition as defined by claim 2, said ionic water-soluble block A also comprising the polymerizate of one or more neutral water-soluble monomers (Ib), selected from among:
   (meth)acrylamide,
   N-vinylacetamide and N-methyl-N-vinylacetamide,
   N-vinylformamide and N-methyl-N-vinylformamide,
   maleic anhydride,
   vinylamine,
   N-vinyllactams containing a cyclic alkyl group having from 4 to 9 carbon atoms,
   vinyl alcohol of formula $CH_2=CHOH$,
   water-soluble vinyl monomers of the following formula (B):

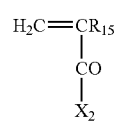

in which $R_{15}$ is H, $-CH_3$, $-C_2H_5$ or $-C_3H_7$ and $X_2$ is selected from among:
(i) alkyl oxides of $-OR_{16}$ type wherein $R_{16}$ is a saturated or unsaturated, linear or branched hydrocarbon radical having from 1 to 6 carbons, optionally substituted with a halogen atom (iodine, bromine, chlorine, fluorine); a hydroxyl group (—OH); an ether group (—O—); a primary amine group (—NH$_2$); a secondary amine group (—NHR$_{17}$) and/or a tertiary amine group (—NR$_{17}$R$_{18}$) in which R$_{17}$ and R$_{18}$, which may be identical or different, are each a saturated or unsaturated, linear or branched hydrocarbon radical having 1 to 6 carbon atoms, provided that the sum of the carbon atoms of R$_{16}$+R$_{17}$+R$_{18}$ does not exceed 6; and (ii) —NH$_2$, —NHR$_{19}$ and —NR$_{19}$R$_{20}$ groups in which R$_{19}$ and R$_{20}$, which may be identical or different, are each a saturated or unsaturated, linear or branched hydrocarbon radical having 1 to 6 carbon atoms, provided that the total number of carbon atoms of R$_{19}$+R$_{20}$ does not exceed 6, said R$_{19}$ and R$_{20}$ being optionally substituted with a halogen atom (iodine, bromine, chlorine, fluorine); a hydroxyl group (—OH); an ether group (—O—); a primary amine group (—NH$_2$); a secondary amine group (—NHR$_{21}$) and/or a tertiary amine group (—NR$_{21}$R$_{22}$) in which R$_{21}$ and R$_{22}$, which may be identical or different, are each a saturated or unsaturated, linear or branched hydrocarbon radical having 1 to 6 carbon atoms, provided that the sum of the carbon atoms of R$_{19}$+R$_{20}$+R$_{21}$+R$_{22}$ does not exceed 6.

4. The photoprotective composition as defined by claim 2, said ionic water-soluble block A also comprising the polymerizate of one or more hydrophobic monomers (Ic), said hydrophobic monomers being present in a sufficiently low quantity for the block A to be soluble in water.

5. The photoprotective composition as defined by claim 4, said hydrophobic monomers (Ic) being selected from among:
styrene and its derivatives,
vinyl acetate of formula CH$_2$=CH—OCOCH$_3$,
vinyl ethers of formula CH$_2$=CHOR in which R is a saturated or unsaturated, linear or branched hydrocarbon radical having from 1 to 6 carbon atoms,
acrylonitrile,
caprolactone,
vinyl chloride and vinylidene chloride,
silicone derivatives,
hydrophobic vinyl monomers of the following formula (C):

in which R$_{23}$ is H, —CH$_3$, —C$_2$H$_5$ or —C$_3$H$_7$ and X$_3$ is selected from among:
(i) alkyl oxides of the —OR$_{24}$ type wherein R$_{24}$ is a saturated or unsaturated, linear or branched hydrocarbon radical having from 1 to 6 carbon atoms; and
(ii) the —NH$_2$, —NHR$_{25}$ and —NR$_{25}$R$_{26}$ groups in which R$_{25}$ and R$_{26}$, which may be identical or different, are each a saturated or unsaturated, linear or branched hydrocarbon radical having 1 to 6 carbon atoms, provided that the total number of carbon atoms of R$_{25}$+R$_{26}$ does not exceed 6.

6. The photoprotective composition as defined by claim 1, said ionic water-soluble block A comprising polyethyleneimine.

7. The photoprotective composition as defined by claim 1, said ionic water-soluble block A being completely or partially neutralized with an inorganic or organic base.

8. The photoprotective composition as defined by claim 7, such neutralization being with an inorganic or organic base selected from among the salts of sodium, ammonium, lithium, calcium or magnesium; ammonium substituted with 1 to 4 alkyl groups having from 1 to 15 carbon atoms, or from mono-, di-, and triethanolamine, aminoethylpropanediol, N-methylglucamine, and basic amino acids and mixtures thereof.

9. The photoprotective composition as defined by claim 1, said hydrophobic block B comprising the polymerizate of hydrophobic monomers (Id) selected from among:
styrene and derivatives thereof,
vinyl acetate of formula CH$_2$=CH—OCOCH$_3$,
vinyl ethers of formula CH$_2$=CHOR' in which R' is a saturated or unsaturated, linear or branched hydrocarbon radical having from 1 to 6 carbons,
acrylonitrile,
vinyl chloride and vinylidene chloride,
caprolactone,
alkenes,
silicone derivatives,
hydrophobic vinyl monomers of the following formula (D):

in which R$_{27}$ is H, —CH$_3$, —C$_2$H$_5$ or —C$_3$H$_7$ and X$_4$ is selected from among:
(i) alkyl oxides of the —OR$_{28}$ type wherein R$_{28}$ is a saturated or unsaturated, linear or branched hydrocarbon radical having from 1 to 22 carbons, optionally substituted with a halogen atom (iodine, bromine, chlorine, fluorine); a sulfonic group (—SO$_3$$^-$); a sulfate group (—SO$_4$$^-$); a phosphate group (—PO$_4$H$_2$$^-$); a hydroxyl group (—OH); an ether group (—O—); a primary amine group (—NH$_2$); a secondary amine group (—NHR$_{29}$) and/or a tertiary amine group (—NR$_{29}$R$_{30}$) or a quaternary amine group (—N$^+$R$_{29}$R$_{30}$R$_{31}$) in which R$_{29}$, R$_{30}$ and R$_{31}$, which may be identical or different, are each a saturated or unsaturated, linear or branched hydrocarbon radical having 1 to 22 carbon atoms, provided that the sum of the carbon atoms of R$_{28}$+R$_{29}$+R$_{30}$+R$_{31}$ does not exceed 22; and
(ii) —NH$_2$, —NHR$_{32}$ and —NR$_{32}$R$_{33}$ groups in which R$_{32}$ and R$_{33}$, which may be identical or different, are each a saturated or unsaturated, linear or branched hydrocarbon radical having 1 to 22 carbon atoms, provided that the total number of carbon atoms of R$_{32}$+R$_{33}$ does not exceed 22, said R$_{32}$ and R$_{33}$ being optionally substituted with a halogen atom (iodine, bromine, chlorine, fluorine); a hydroxyl group (—OH); an ether group (—O—); a sulfonic group (—SO$_3$$^-$); a sulfate group (—SO$_4$$^-$); a phosphate group (—PO$_4$H$_2$$^-$); a primary amine group (—NH$_2$); a secondary amine group (—NHR$_{34}$) and/or a tertiary amine group (—NR$_{34}$R$_{35}$) and/or a quaternary amine group (—N$^+$R$_{34}$R$_{35}$R$_{36}$) in which R$_{34}$, R$_{35}$ and R$_{36}$, which may be identical or different, are each a saturated or unsaturated, linear or branched hydrocarbon radical having 1 to 22 carbon atoms, provided that the sum of the carbon atoms of $R_{32}+R_{33}+R_{34}+R_{35}+R_{36}$ does not exceed 22 and further wherein $R_{32}$ and $R_{33}$ may also be a perfluoroalkyl radical.

10. The photoprotective composition as defined by claim 9, said hydrophobic block B also comprising the polymerizate of one or more water-soluble monomers (Ie) and their salts; said water-soluble monomers being present in a sufficiently low quantity for the block B to be hydrophobic.

11. The photoprotective composition as defined by claim 10, said water-soluble monomers (Ie) being selected from among:
(meth)acrylic acid,
styrenesulfonic acid,
vinylsulfonic acid and (meth)allylsulfonic acid,
vinylphosphonic acid,
maleic acid and anhydride,
itaconic acid,
crotonic acid,
dimethyldiallylammonium chloride,
methylvinylimidazolium chloride,
(meth)acrylamide,
N-vinylacetamide and N-methyl-N-vinylacetamide,
N-vinylformamide and N-methyl-N-vinylformamide,
N-vinyllactams containing a cyclic alkyl group having from 4 to 9 carbon atoms,
the vinyl alcohol of formula $CH_2=CHOH$,
2-vinylpyridine and 4-vinylpyridine,
water-soluble vinyl monomers of the following formula (E):

in which $R_{37}$ is H, $-CH_3$, $-C_2H_5$ or $-C_3H_7$ and $X_5$ is selected from among:
(i) alkyl oxides of the $-OR_{38}$ type wherein $R_{38}$ is a saturated or unsaturated, linear or branched hydrocarbon radical having from 1 to 6 carbon atoms, optionally substituted with a halogen atom (iodine, bromine, chlorine, fluorine); a sulfonic group ($-SO_3^-$); a sulfate group ($-SO_4^-$); a phosphate group ($-PO_4H_2^-$); a hydroxyl group ($-OH$); an ether group ($-O-$); a primary amine group ($-NH_2$); a secondary amine group ($-NHR_{39}$)and/or a tertiary amine group ($-NR_{39}R_{40}$) or a quaternary ammonium group ($-N^+R_{39}R_{40}R_{41}$) in which $R_{39}$, $R_{40}$ and $R_{41}$, which may be identical or different, are each a saturated or unsaturated, linear or branched hydrocarbon radical having 1 to 6 carbon atoms, provided that the sum of the carbon atoms $R_{38}+R_{39}+R_{40}+R_{41}$ does not exceed 6; and
(ii) $-NH_2$, $-NHR_{42}$ and $-NR_{42}R_{43}$ groups in which $R_{42}$ and $R_{43}$, which may be identical or different, are each a saturated or unsaturated, linear or branched hydrocarbon radical having 1 to 6 carbon atoms, provided that the total number of carbon atoms of $R_{42}+R_{43}$ does not exceed 6, said $R_{42}$ and/or $R_{43}$ being optionally substituted with a halogen atom (iodine, bromine, chlorine, fluorine); a sulfonic group ($-SO_3^-$); a sulfate group ($-SO_4^-$); a phosphate group ($-PO_4H_2^-$); a hydroxyl group ($-OH$); an ether group ($-O-$); a primary amine group ($-NH_2$); a secondary amine group ($-NHR_{44}$) and/or a tertiary amine group ($-NR_{44}R_{45}$)or a quaternary amine group ($-N^+R_{44}R_{45}R_{46}$) in which $R_{44}$, $R_{45}$ and $R_{46}$, which may be identical or different, are each a saturated or unsaturated, linear or branched hydrocarbon radical having 1 to 6 carbon atoms, provided that the sum of the carbon atoms of $R_{42}+R_{43}+R_{44}+R_{45}+R_{46}$ does not exceed 6.

12. The photoprotective composition as defined by claim 1, said diblock or triblock polymer having a molar mass ranging from 1,000 g/mol to 500,000 g/mol.

13. The photoprotective composition as defined by claim 1, said ionic water-soluble block A having a molar mass ranging from 600 g/mol to 300,000 g/mol.

14. The photoprotective composition as defined by claim 1, said hydrophobic block B having a molar mass ranging from 400 g/mol to 200,000 g/mol.

15. The photoprotective composition as defined by claim 1, the proportion by mass of the ionic hydrophilic block A in the diblock polymers A-B being greater than 60%.

16. The photoprotective composition as defined by claim 1, the proportion by mass of the ionic hydrophilic block A in the triblock polymers B-A-B being greater than 50%.

17. The photoprotective composition as defined by claim 1, the diblock or triblock polymers comprising an ionic water-soluble polymeric block A which is completely water-soluble and hydrophobic polymeric blocks B which are completely hydrophobic.

18. The photoprotective composition as defined by claim 1, said diblock polymers comprising polystyrene/sodium polyacrylate diblock polymers.

19. The photoprotective composition as defined by claim 18, the diblock polymer comprising:
the polystyrene (2,000 g/mol)-sodium polyacrylate (11,500 g/mol) diblock polymer wherein the water-soluble ionic block (sodium polyacrylate) constitutes 85.2% of the total weight of the diblock polymer;
the polystyrene (1,800 g/mol)-sodium polyacrylate (42,450 g/mol) diblock polymer wherein the water-soluble ionic block (sodium polyacrylate) constitutes 95.9% of the total weight of the diblock polymer; or
the polystyrene (4,300 g/mol)-sodium polyacrylate (25,460 g/mol) diblock polymer wherein the water-soluble ionic block constitutes 85.55% of the total weight of the diblock copolymer.

20. The photoprotective composition as defined by claim 1, the triblock polymers comprising polystyrene/sodium polyacrylate/polystyrene triblock polymers.

21. The photoprotective composition as defined by claim 20, the triblock polymer comprising the polystyrene (2,500 g/mol)-sodium polyacrylate (29,800 g/mol)-polystyrene (2,500 g/mol) triblock polymer wherein the quantity of water-soluble block constitutes 85.63% of the total weight of the triblock copolymer.

22. The photoprotective composition as defined by claim 1, wherein the concentration by mass of the diblock or triblock polymer in the composition ranges from 0.01% to 30% by weight relative to the total weight of the composition.

23. The photoprotective composition as defined by claim 1, said at least one 4,4-diarylbutadiene UV-A-screening agent having the following formula (II):

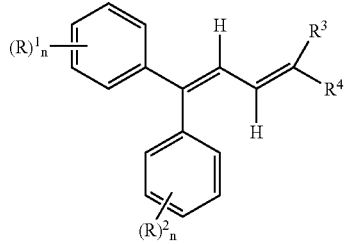

(II)

in which the diene system is of the Z,Z; Z,E; E,Z or E,E configuration or mixture of said configurations, and wherein:

$R^1$ and $R^2$, which may be identical or different, are each hydrogen, a $C_1$-$C_{20}$ alkyl radical, a $C_2$-$C_{10}$ alkenyl radical, a $C_1$-$C_{12}$ alkoxy radical, a $C_3$-$C_{10}$ cycloalkyl radical, a $C_3$-$C_{10}$ cycloalkenyl radical, a $C_1$-$C_{20}$ alkoxycarbonyl radical, a $C_1$-$C_{12}$ monoalkylamino radical, a $C_1$-$C_{12}$ dialkylamino radical, an aryl radical, a heteroaryl radical or a water-solubilizing substituent selected from among a carboxylate residue, a sulfonate residue or an ammonium residue;

$R^3$ is a group $COOR^5$, $COR^5$, $CONR^5R^6$, CN, O=S(—$R^5$)=O, O=S(—$OR^5$)=O, $R^7$O—P—(—$OR^8$)=O, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$C_{18}$ aryl radical, an optionally substituted $C_3$-$C_7$ heteroaryl radical;

$R^4$ is a group $COOR^6$, $COR^6$, $CONR^5R^6$, CN, O=S(—$R^6$)=O, O=S(—$OR^6$)=O, $R^7$O—P—(—$OR^8$)=O, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ cycloalkenyl radical, a $C_7$-$C_{10}$ bicycloalkenyl radical, an optionally substituted $C_6$-$C_{18}$ aryl radical, an optionally substituted $C_3$-$C_7$ heteroaryl radical;

the radicals $R^5$ to $R^8$, which may be identical or different, are each hydrogen, a $C_1$-$C_{20}$ alkyl radical, a $C_2$-$C_{10}$ alkenyl radical, a $C_3$-$C_{10}$ cycloalkyl radical, a $C_7$-$C_{10}$ bicycloalkyl radical, a $C_3$-$C_{10}$ bicycloalkenyl radical, a $C_7$-$C_{10}$ cycloalkenyl radical, an optionally substituted aryl radical, an optionally substituted heteroaryl radical, and n ranges from 1 to 3; with the proviso that the radicals $R^3$ to $R^8$ can together form, with the carbon atoms from which they depend, a $C_5$-$C_6$ ring which may be fused.

24. The photoprotective composition as defined by claim 23, wherein formula (II):

n=1 or 2;

$R^1$ and $R^2$, which may be identical or different, are each hydrogen, a $C_1$-$C_{20}$ alkyl radical, a $C_1$-$C_{12}$ alkoxy radical, a $C_1$-$C_{12}$ monoalkylamino radical, a $C_1$-$C_{12}$ dialkylamino radical, a water-solubilizing substituent selected from among oxylate group, a sulfonate group or an ammonium residue;

$R^3$ is a group $COOR^5$, $COR^5$, $CONR^5R^6$, a $C_1$-$C_{20}$ alkyl radical, a $C_3$-$C_{10}$ cycloalkyl radical, a $C_3$-$C_{10}$ cycloalkenyl radical, a $C_7$-$C_{10}$ bicycloalkyl radical, optionally substituted phenyl, naphthyl or thienyl;

$R^4$ is a group $COOR^6$, $COR^6$, $CONR^5R^6$, a $C_1$-$C_{20}$ alkyl radical, a $C_3$-$C_6$ cycloalkyl radical, a $C_3$-$C_{10}$ cycloalkenyl radical, a $C_7$-$C_{10}$ bicycloalkyl radical, optionally substituted phenyl, naphthyl or thienyl;

the radicals $R^5$ and $R^6$, which may be identical or different, are each hydrogen, a $C_1$-$C_{12}$ alkyl radical, a $C_3$-$C_{10}$ cycloalkyl radical, a $C_3$-$C_{10}$ cycloalkenyl radical, a $C_7$-$C_{10}$ bicycloalkyl radical, a $C_3$-$C_{10}$ bicycloalkenyl radical, optionally substituted phenyl or naphthyl.

25. The photoprotective composition as defined by claim 24, wherein formula (II):

$R^1$ and $R^2$, which may be identical or different, are each hydrogen, a $C_1$-$C_{20}$ alkyl radical, a $C_1$-$C_{20}$ alkoxy radical, a water-solubilizing substituent selected from among a carboxylate group, a sulfonate group or an ammonium residue;

$R^3$ is a group $COOR^5$, $COR^5$, $CONR^5R^6$;

$R^4$ is a group $COOR^6$, $COR^6$, $CONR^5R^6$; and the radicals $R^5$ and $R^6$, which may be identical or different, are each hydrogen, a $C_1$-$C_{12}$ alkyl radical, a $C_3$-$C_6$ cycloalkyl radical, a $C_3$-$C_{10}$ cycloalkenyl radical, a $C_7$-$C_{10}$ bicycloalkyl radical, a $C_3$-$C_{10}$ bicycloalkenyl radical, optionally substituted phenyl or naphthyl.

26. The photoprotective composition as defined by claim 25, said at least one compound of formula (II) having the following formula (II'):

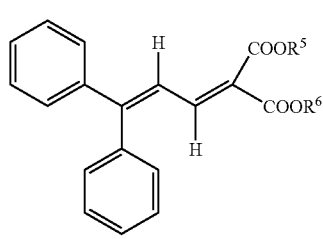

(II')

wherein the radicals $R^5$ and $R^6$, which may be identical or different, are each hydrogen, a $C_1$-$C_{20}$ alkyl radical, a $C_3$-$C_6$ cycloalkyl radical, a $C_3$-$C_{10}$ cycloalkenyl radical.

27. The photoprotective composition as defined by claim 26, the compound of formula (II') being the 1,1-dicarboxy (2'2'-dimethylpropyl)-4,4-diphenylbutadiene derivative having the structure:

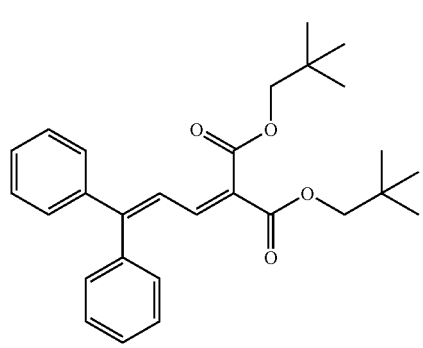

(compound f)

28. The photoprotective composition as defined by claim 1, said at least one 4,4-diarylbutadiene UV-A-screening agent having the following formula (III):

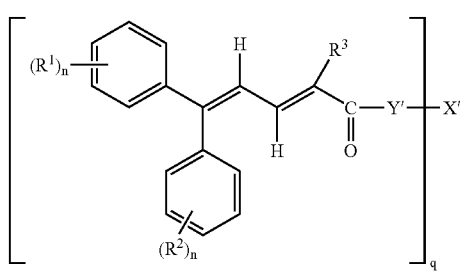

(III)

in which the diene system is of the Z,Z; Z,E; E,Z or E,E configuration or mixture of said configurations and wherein:

R$^1$, R$^2$, R$^3$ and n have the meanings indicated in the formula (II);

Y' is a group —O— or —NR$^9$—;

R$^9$ is hydrogen, a linear or branched C$_1$-C$_{20}$ alkyl radical, a C$_2$-C$_{10}$ alkenyl radical, a C$_3$-C$_{10}$ cycloalkyl radical, a C$_7$-C$_{10}$ bicycloalkyl radical, a C$_3$-C$_{10}$ cycloalkenyl radical, a C$_7$-C$_{10}$ bicycloalkenyl radical, an aryl radical, a heteroaryl radical;

X' is a residue of a linear or branched, aliphatic or cycloaliphatic C$_2$-C$_{20}$ polyol comprising from 2 to 10 hydroxyl groups and having the valency q; with the proviso that the carbon chain of said residue may be interrupted by one or more sulfur or oxygen atoms, one or more imine groups, one or more C$_1$-C$_4$ alkylimino groups; and q ranges from 2 to 10.

29. The photoprotective composition as defined by claim 28, wherein formula (III):

R$^1$ and R$^2$, which may be identical or different, are each hydrogen, a C$_1$-C$_{12}$ alkyl radical, a C$_1$-C$_8$ alkoxy radical, a water-solubilizing substituent selected from among a carboxylate group, a sulfonate group or an ammonium residue;

R$^3$ is a group COOR$^5$, CONR$^5$R$^6$, CN, a C$_3$-C$_{10}$ cycloalkyl radical, a C$_7$-C$_{10}$ bicycloalkyl radical;

R$^5$ and R$^6$, which may be identical or different, are each a linear or branched C$_1$-C$_{20}$ alkyl radical, a C$_3$-C$_{10}$ cycloalkyl radical, a C$_7$-C$_{10}$ bicycloalkyl radical, optionally substituted naphthyl or phenyl; and X' is a C$_2$-C$_{20}$ polyol residue comprising from 2 to 6 hydroxyl groups.

30. The photoprotective composition as defined by claim 28, wherein formula (III), X' is an ethanol or pentaerythritol residue.

31. The photoprotective composition as defined by claim 30, said at least one compound of formula (III) being selected from among the following compounds:

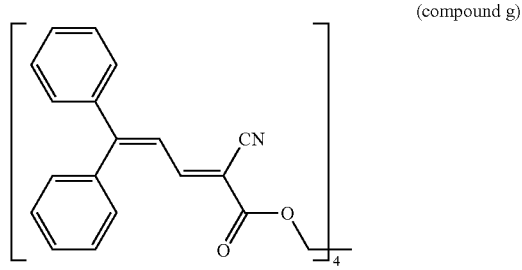

(compound g)

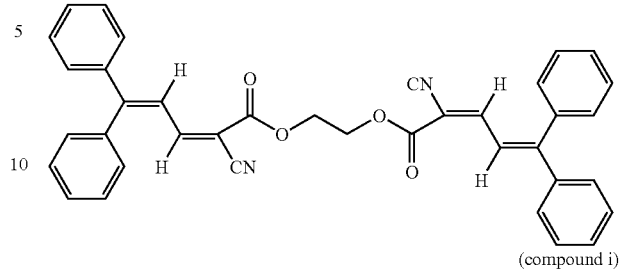

(compound h)

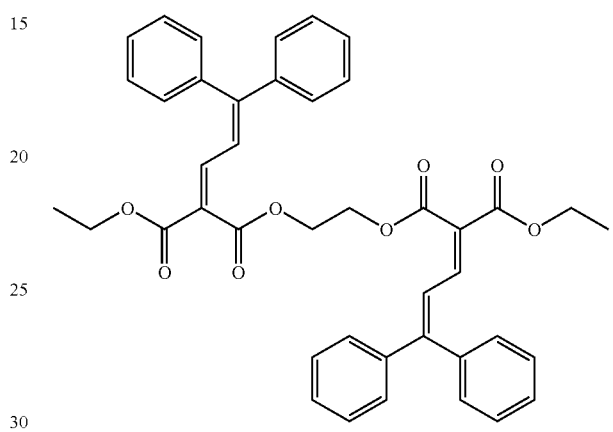

(compound i)

32. The photoprotective composition as defined by claim 1, said at least one 4,4-diarylbutadiene compound comprising from 0.1% to 20% by weight relative to the total weight of the composition.

33. The photoprotective composition as defined by claim 1, further comprising at least one additional organic or inorganic sunscreening agent active in the UV-A and/or UV-B regions, water-soluble, fat-soluble or insoluble in the commonly used cosmetic solvents.

34. The photoprotective composition as defined by claim 33, comprising at least one additional organic screening agent selected from among the anthranilates; cinnamic derivatives; dibenzoylmethane derivatives; salicylic derivatives, camphor derivatives; triazine derivatives; benzophenone derivatives; β,β'-diphenyl acrylate derivatives; benzotriazole derivatives; benzalmalonate derivatives; benzimidazole derivatives; imidazolines; bis-benzoazolyl derivatives; p-aminobenzoic acid (PABA) derivatives; benzoxazole derivatives; methylenebis(hydroxyphenylbenzotriazole) derivatives; screening polymers and screening silicones; dimers derived from α-alkylstyrene and mixtures thereof.

35. The photoprotective composition as defined by claim 34, said at least one additional organic screening agent comprising:

Ethylhexyl Salicylate,
Ethylhexyl Methoxycinnamate,
Octocrylene,
Butyl Methoxydibenzoylmethane,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene camphor, Terephthalylidene Dicamphor Sulfonic acid,
Disodium Phenyl Dibenzimidazole Tetra-sulfonate,
2,4,6-Tris(4'-diisobutyl aminobenzalmalonate)S-triazine
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone 15,
2,4-Bis-[5-1-(dimethylpropyl)benzoxazol-2-yl-(4-phenyl)imino]-6-(2-ethylhexyl)imino-1,3,5-triazine, and mixtures thereof.

36. The photoprotective composition as defined by claim 33, comprising at least one additional inorganic screening agent selected from among metal oxide pigments or nanopigments, whether coated or uncoated.

37. The photoprotective composition as defined by claim 33, said at least one additional inorganic screening agent comprising nanopigments of titanium oxide, which is amorphous or crystallized, in rutile and/or anatase form, iron oxide, zinc oxide, zirconium oxide or cerium oxide.

38. The photoprotective composition as defined by claim 1, further comprising at least one agent for artificial bronzing and/or tanning of the skin.

39. The photoprotective composition as defined by claim 1, further comprising at least one cosmetic adjuvant selected from among organic solvents, ionic or nonionic thickeners, demulcents, humectants, active agents, opacifying agents, stabilizers, emollients, silicones, insect repellents, perfumes, preservatives, surfactants, fillers, pigments, polymers, propellants, alkalinizing or acidifying agents or any other ingredient commonly employed in the cosmetic and/or dermatological field.

40. The photoprotective composition as defined by claim 1, formulated as a lotion or serum with no fatty phase, an oil-in-water or water-in-oil emulsion, a multiple emulsion, a microemulsion, a vesicular dispersion of the ionic and/or nonionic type, or of a wax/aqueous phase dispersion.

41. The photoprotective composition as defined by claim 1, formulated as an oil-in-water or water-in-oil emulsion containing at most 1% by weight of emulsifying surfactant relative to the total weight of the composition.

42. A method for the photoprotection of the skin, lips and/or hair against the damaging effects of UV-radiation, comprising topically applying thereon, a thus effective amount of a photoprotective composition comprising at least one aqueous phase, at least one water-soluble or water-dispersible polymer having a diblock structure A-B or a triblock structure B-A-B wherein A is an ionic water-soluble polymeric block and B is a hydrophobic polymeric block and at least one system screening out UV radiation, said at least one screening system comprising at least one 4,4-diarylbutadiene UV-A screening agent.

* * * * *